United States Patent
Khalsa et al.

[11] Patent Number: 5,575,295
[45] Date of Patent: Nov. 19, 1996

[54] METHOD AND APPARATUS FOR RESTORING SPINAL CERVICAL CURVATURE

[75] Inventors: Guruchander S. Khalsa, Espanola; Muktiar S. Khalsa, Santa Cruz, both of N.M.

[73] Assignee: Chiro-Yog, Inc., Santa Fe, N.M.

[21] Appl. No.: 844,711

[22] Filed: Mar. 2, 1992

[51] Int. Cl.⁶ ............................................. A61G 15/00
[52] U.S. Cl. .............................. 128/845; 5/646; 602/18
[58] Field of Search .............................. 27/13, 12, 25; 602/40, 17, 18; 606/238, 240; 128/870, 845, 846; 5/636, 643, 646, 648

[56] References Cited

U.S. PATENT DOCUMENTS

| | | | |
|---|---|---|---|
| 1,625,267 | 4/1927 | Masters | 27/13 |
| 1,973,240 | 9/1934 | Werness | 5/648 |
| 2,478,597 | 8/1949 | Scarpellino | 5/636 |
| 3,748,705 | 7/1973 | Deaton | 27/13 |
| 3,799,534 | 3/1974 | Coles | 27/13 |
| 3,949,437 | 4/1976 | Gritsch | 5/643 |
| 4,166,459 | 9/1979 | Nightingale | 5/636 |
| 4,681,309 | 7/1987 | Lechner | 5/646 |
| 4,803,743 | 2/1989 | Greenawalt | 5/636 |
| 4,832,007 | 5/1989 | Davis | 5/636 |
| 5,033,137 | 7/1991 | Pedrow | 5/636 |

Primary Examiner—Michael A. Brown
Attorney, Agent, or Firm—Wolf, Greenfield & Sacks P.C.

[57] ABSTRACT

A method and apparatus for restoring spinal cervical curvature by having the patient lie on his back on a surface with his neck at the C3/C6 vertebra positioned in the groove formed in the top of a block of a substantially non-deformable material supported in an upright position on the surface. The width of the groove is greater than the width of the patient's neck, and the thickness of the block at least at the top surface is generally in the range of ½ inch to 3 inches. The height of the groove at its lowest position is sufficient so that the patient's head is supported above the surface, but is not so great as to be uncomfortable for the patient. The patient remains in this position for several minutes and the treatment is repeated preferably three times a day for a period of several months.

13 Claims, 1 Drawing Sheet

METHOD AND APPARATUS FOR RESTORING SPINAL CERVICAL CURVATURE

FIELD OF THE INVENTION

This invention relates to a method and apparatus for spinal therapy in the cervical area and more particularly to a method and apparatus for restoring spinal cervical curvature.

BACKGROUND OF THE INVENTION

A common disorder treated by both orthopedists and chiropractors results from the normal concave inward curve of the cervical spine becoming either straight or reversing so as to curve outward. This condition can result from a hyperextension injury such as a "whiplash" injury resulting from an automobile accident or the like or may be caused by the patient's life-style. Life-style causes for such injuries include occupations such as model or the military which require stiff or rigid posture or professions which require the patient to look down all day such as draftsmen or architects. Such spinal cervical curve disorders can be extremely painful for the patient, particulary where it causes a blocking of the spinal cord opening, resulting in pinched nerves. If this condition is not corrected, it can result in spinal degeneration, further adding to the patient's discomfort. Further, this condition can also cause moderate to severe distortion of nerve function which may result in swelling of limbs, particularly arms and hands, and in a degradation in the patient's ability to use such limbs.

Current therapies for such disorders have been primarily directed at easing the patient's pain, but have not resulted in the muscle retraining in the cervical area required to restore normal neck curvature and to unblocking the foraminal stenosis. Thus, these current therapies, which include traction devices, and soft or semi-soft pillows, are only effective in somewhat easing the patient's pain; they are not effective in either correcting the problem resulting in the pain or in completely eliminating the pain.

A need, therefore, exists for an improved method and apparatus for treating spinal cervical curve disorders, and in particular for a method and apparatus which permits substantially normal cervical curve to be restored in such patients along with unblocking of the spinal cord cavity.

With the current problem of exploding medical costs, it is also desirable that this method and apparatus be relatively inexpensive both to fabricate and to use, and that it be possible for the treatment to be performed on an outpatient basis, preferably in the patient's home. Further, both for reasons of costs and patient comfort, it is desirable that results from the therapy be achievable within a reasonable time frame.

SUMMARY OF THE INVENTION

In accordance with the above, this invention provides a method and apparatus for restoring spinal cervical curvature which permits such objective to be achieved utilizing an inexpensive apparatus and a method which may be practiced on an outpatient basis or at home by the patient with periodic visits to a doctor or chiropractor. Utilizing the teachings of this invention, substantially normal spinal cervical curvature can generally be restored within several months.

More particular, the apparatus of this invention includes a block formed of a material which is substantially non-deformable when pressure is applied thereto. The block has a curved groove formed in its top surface, the width of the groove being greater than the width of the patient's neck. The block has a thickness at least at its top surface which is generally ½" to 3", a thickness which is normally substantially the same as the extent of one to three cervical vertebra of the patient. The block is supported at its bottom portion in an upright position on a generally horizontal surface. The dimensions of the apparatus are such that, when the patient is lying on his back on the surface with the area of the patient's neck of the C3/C6 vertebra position in the groove, the patient's head is supported above the surface. In particular, the groove has a lowest point at approximately the center of the block with the dimensions of the apparatus being such that the distance from such lowest point to the surface are sufficient to support the patient's head above the surface, but not so great as to be uncomfortable for the patient. For preferred embodiments, this distance is approximately 3½ to 4½ inches. A layer of deformable material is preferably included in the groove in at least the area thereof in contact with the patient's neck. The layer is preferably a strip of a deformable material secured in the groove, but may also be achieved by forming the block of material with non-uniform deformability, with the material being more deformable in the area of the groove and substantially non-deformable in other areas.

The block may be supported in the desired upright position by having the lower part of the block be wider than the top surface to provide the desired support. However, particularly where the apparatus is to be portable, it is preferable that the apparatus include a base with the block being mounted on the base. In order to provide the desired support, the extent of the base in the dimension of block thickness should be greater than the block thickness. For portability, it is desirable that the extent of the apparatus in such thickness dimension be reduced when the apparatus is not in use to permit the apparatus to be easily packed. For preferred embodiments, this may be accomplished by fabricating the apparatus such that the block and base are easily assembled and disassembled.

Spinal cervical curvature restoration is achieved by having the patient lie on his back with the area of the patient's neck at the C3/C6 vertebra positioned in the groove of the block, the block supporting the patient's neck such that the patient's head is held above the surface, and the patient remains in this position for several minutes. For a preferred embodiment, the patient remains in this position for approximately five minutes. This therapy of lying on the apparatus is preferably repeated approximately three times a day over a period of several months. The restoring of substantially normal spinal cervical curvature can generally be accomplished over a period of approximately three months. It is preferable that standard chiropractic neck treatments be performed on the patient at the same time that the patient is undergoing the therapy of this invention in order to achieve optimum results.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
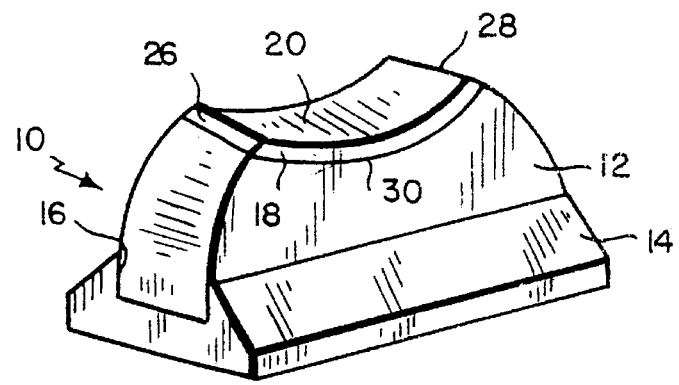
FIG. 1 is a top front perspective view of therapeutic apparatus of a preferred embodiment of the invention.

Referring first to FIG. 1, the apparatus 10 for a preferred embodiment of the invention comprises a block 12 of a material which does not substantially deform when pressure is applied thereto which block is mounted to a base 14. Suitable materials for block 12 are soft woods such as pine, hardwoods, plastic, various metals, stone, ceramic, and the like. Typically, block 12 would be solid. However, where a material having sufficient strength and rigidity is employed, such as a metal, so that the block will not substantially deform under pressure, the block may also be hollow. It is also possible for block 12 to be formed of a watertight or airtight bladder in the appropriate shape which is filled with a liquid or gas to a sufficient pressure so as to have the requisite hardness.

Base 14 may be formed of the same material as block 12, or may be formed of a different material. For embodiments where the apparatus 10 is to be used at a single location, and there is no need for the apparatus to be portable, elements 12 and 14 may be permanently affixed together, for example by gluing, nailing, screwing, or some combination thereof. However, in applications where the apparatus 10 is to be carried from one place to another, for example where the apparatus is given to a patient to take home with him, or where the patient may be periodically visited by a therapist, the apparatus 10 in assembled form may be too bulky for easy packing. It is, therefore, desirable in such applications that the user be able to assemble and disassemble the block and base. In FIG. 1, this is accomplished by providing a groove 16 in base 14 in which block 12 may be fitted from the top or slid in from the side. Various techniques known in the art may be utilized to assure proper orientation of the parts when assembled and, if desired, to assure that the parts do not spuriously separate. However, since in use pressure is applied to the top of the block, the parts once assembled should not separate in ordinary use.

Block 12 has a curved groove 18 formed in its top surface. A strip 20 of a soft, deformable material such as closed cell foam is secured in groove 18 by glue, double-sided tape, or other suitable means. Strip 20 is preferably relatively thin, ½" to 1" for a preferred embodiment, and is not required for the therapeutic function of the block. The strip is included only to enhance patient comfort, and if thin enough, can achieve this objective without substantial adverse therapeutic effect.

Figure 2:
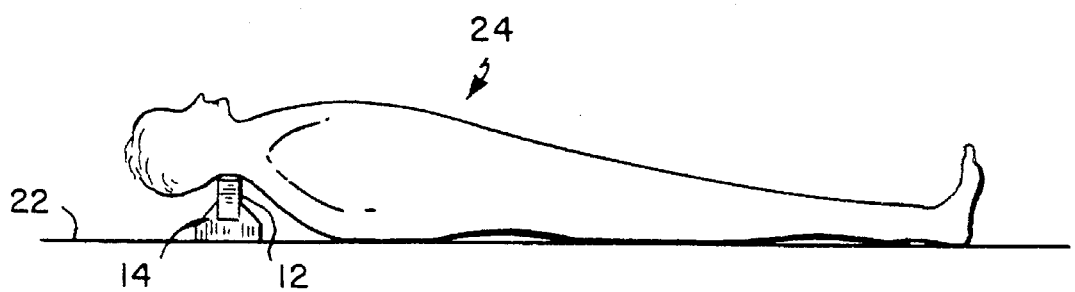
FIG. 2 is a side view illustrating the apparatus of FIG. 1 in use on a patient.

As shown in FIG. 2, base 14 supports block 12 in an upright position on a surface 22. Surface 22 is preferably a substantially flat horizontal surface such as a floor or table. The width of groove 18, with strip or pad 20 secured therein is sufficient so that the neck of a patient 24 being treated can fit therein. A width of approximately 7 inches between points 26 and 28 has been found suitable for most individuals; however, a greater width may be required for people having a particularly thick neck. The thickness of block 12 at groove 18 is another reasonably important dimension. This width should be approximately equal to the extent of one to three spinal cervical vertebra for the patient. Typically, this would be approximately 1½ inches, although this may again vary somewhat depending on the size of the individual. Widths for the block in the groove area of approximately ½ inch to 3 inches would normally provide satisfactory results.

A third important dimension is the height from the point 30, which is the lowest point of groove 18 to surface 22. Since the material of strip 20 is normally compressible, and is very thin to begin with, the thickness of this strip is not normally taken into account in determining this dimension. This height should be sufficient such that the head of the patient is supported by apparatus 10 above surface 22, as shown in FIG. 2, but should not be so high as to cause the patient's shoulders to be significantly raised off the surface. Stated another way, the height to the low point 30 should be sufficient so that a significant portion of the patient's weight is borne by apparatus 10, but no so high that the pressure on the back of the patient's neck causes discomfort. It has been found that a height to point 30 of approximately 3½ to 4½ inches generally achieves the above objectives.

In use, the apparatus 10 is positioned on surface 22 with block 12 in an upright position and the patient lays on surface 12 with the portion of his neck in the area of the C3/C6 spinal cervical vertebra resting in groove 18. When the patient is lying in this position, enough pressure is applied to the vertebra to push them back into the desired inward concave position. The patient remains in this position for approximately five minutes and preferably repeats the procedure three times a day for several months. This results in a retraining of the patient's muscles in the cervical area. It is desirable that, while the patient is undergoing the therapy indicated above, the patient is also receiving standard chiropractic corrections and treatment for neck problems. Neck exercises may also be useful and, to the extent the condition is life-style related, an alternation in the life-style which created the problem is also desirable. When these conditions are fulfilled, it has been found that a 40 to 80% correction of the cervical curve defect can generally be achieved within three months. Further treatment can result in additional correction. The treatment also results in the unblocking of the spinal cord cavity, thus relieving pressure on pinched nerves and in a dramatic reduction, frequently to zero or near zero, in the pain being experienced by the patient. These improvements are even achievable where the condition has existed for some time and has become chronic and is the first successful treatment for long-standing foraminal stenosis.

Figure 3:
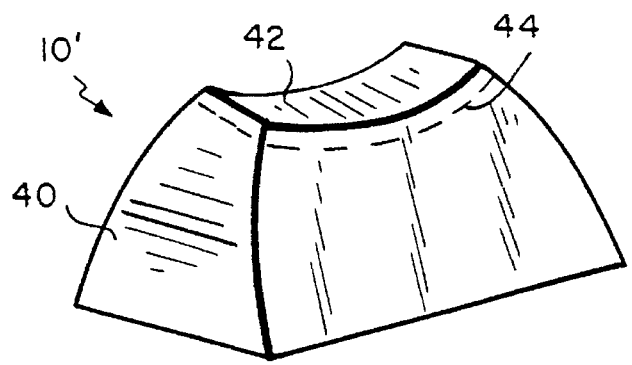
FIG. 3 is a top front perspective view of an alternative embodiment of the invention.

FIG. 3 illustrates an alternative embodiment of the invention which is primarily suitable for use in a single location rather than being portable. In this case, the apparatus 10' is formed of a single block 40 which has the required width previously discussed in the area of a groove 42 formed therein, but is substantially wider at its base to provide stable support for the apparatus in its upright position. The sides of the block 40 may project at an angle as shown in FIG. 3 or may have a curved shape, for example, a parabolic curve, so that the block remains substantially at the required width at the groove for some extent of the block before curving out on both sides to form the wide supporting base.

For the embodiment of FIG. 3, it is also assumed that the block is formed, for example molded, of a plastic. In this illustrative embodiment, the lower portion of the block is formed of a hard material required for the therapeutic process while a thin band 44 near the groove is formed of a softer plastic, for example, a cellular plastic, to enhance patient comfort. With this arrangement, strip 20 is not required.

While several shapes of apparatus have been shown and described above, it is apparent that the exact shape of the block, and of the base where used, are not critical so long as functional dimensions discussed above are maintained. Further, while for the preferred embodiment the bulk of the apparatus for purposes of packing has been reduced by having the block and base be easily disassembled, similar results could be achieved by replacing base 14 with, for example, two pairs of legs which could be pivoted out when the block is in use and folded into the base of the block or under the base of the block when the apparatus is to be packed. The base could also be hinged on each side so as to be foldable up against the block, or could be otherwise formed to achieve the desired objective. Where the block is in the form of a bladder filled with a liquid or gas under pressure, the apparatus can be made very small and light for transportation by emptying the bladder. However, the problem of refilling the bladder to the desired pressure may make this a less desirable alternative.

Thus, while the invention has been particularly shown and described above with reference to preferred embodiments, the foregoing and other changes in form and detail may be made therein by one skilled in the art without departing from the spirit and scope of the invention.

What is claimed is:

1. Apparatus for use in restoring spinal cervical curvature in a patient's neck comprising;

a block formed of a material which is substantially non-deformable when pressure is applied thereto, said block having a top surface, a curved groove formed in said top surface, the width of said groove being greater than the width of the patient's neck, a bottom section, and a thickness at least at said top surface which is generally in the range of ½" to 3", said groove having a lowest point at approximately the center of the groove, the distance from said lowest point to the surface being approximately 3½ to 4½ inches, means for supporting the block in an upright position on a generally horizontal surface; the dimensions of the apparatus being such that, when the patient is laying on his back with the area of the patient's neck of the C3/C6 vertebra positioned in the groove, the patient's head is supported above the surface.

2. Apparatus as claimed in claim 1 including a layer of deformable material in said groove at least in the area thereof in contact with the patient's neck.

3. Apparatus as claimed in claim 2 wherein said layer is a strip of deformable material secured in said groove.

4. Apparatus as claimed in claim 3 wherein said strip is formed of a foam material.

5. Apparatus as claimed in claim 2 wherein said block is formed of material with non-uniform deformability, the material being more deformable in the area of said groove and substantially non-deformable in other areas.

6. Apparatus as claimed in claim 1 wherein said means for supporting is formed as part of said block, the lower portion of the block being wider than the top surface.

7. Apparatus as claimed in claim 1 wherein said means for supporting includes a base, and means for mounting the block on the base, the extent of said base in the dimensions of the block thickness being greater than said thickness.

8. Apparatus as claimed in claim 7 including means for permitting the extent of the apparatus in said thickness dimension to be reduced when the apparatus is not in use, whereby the apparatus may be more easily packed.

9. Apparatus as claimed in claim 8 wherein said means for permitting includes means for facilitating the assembly and disassembly of the block and base.

10. A method for restoring spinal cervical curvature in a patient's neck comprising the steps of:

a) providing a block formed of a material which is substantially non-deformable when pressure is applied thereto, said block having a top surface, a curved groove formed in said top surface, the width of said groove being greater than the width of the patient's neck, a bottom section, and a thickness at least at said top surface which is generally in the range of ½" to 3";

b) supporting the block in an upright position on a generally horizontal surface;

c) having the patient lie on his back with the area of the patient's neck of the C3/C6 vertebra positioned in the groove, the block supporting the patient's neck such that the patient's head is held above the surface, step (c) being performed for several minutes; and d) repeating steps (a)–(c) approximately three times a day for a period of several months.

11. A method as claimed in claim 10 wherein step (c) is performed for approximately five minutes.

12. A method as claimed in claim 10 wherein step (d) is repeated for a period of approximately three months.

13. A method as claimed in claim 10 including the steps of performing chiropractic neck treatments on the patient during the period step (d) is repeated.

* * * * *